(12) United States Patent
Mehta (10) Patent No.: US 11,883,589 B2
(45) Date of Patent: Jan. 30, 2024

(54) TRACHEOSTOMY TUBE MONITOR AND ALERTING APPARATUS

(71) Applicant: Deepak Kumar Mehta, Sugar Land, TX (US)

(72) Inventor: Deepak Kumar Mehta, Sugar Land, TX (US)

(*) Notice: Subject to any disclaimer, the term of this patent is extended or adjusted under 35 U.S.C. 154(b) by 1052 days.

(21) Appl. No.: 16/457,175

(22) Filed: Jun. 28, 2019

(65) Prior Publication Data

US 2020/0001028 A1 Jan. 2, 2020

Related U.S. Application Data

(60) Provisional application No. 62/692,026, filed on Jun. 29, 2018.

(51) Int. Cl.
*A61M 16/00* (2006.01)
*A61M 16/10* (2006.01)
(Continued)

(52) U.S. Cl.
CPC .... *A61M 16/0051* (2013.01); *A61M 16/0465* (2013.01); *A61M 16/0816* (2013.01); *A61M 16/105* (2013.01); *A61M 16/1045* (2013.01); *A61M 16/161* (2014.02); *A61M 2016/0027* (2013.01); *A61M 2016/0036* (2013.01);
(Continued)

(58) Field of Classification Search
CPC .......... A61M 16/0051; A61M 16/0465; A61M 16/0816; A61M 16/085; A61M 16/1045; A61M 16/0875; A61M 16/105; A61M 16/161; A61M 2016/0036; A61M 2205/3576; A61M 2205/50; A61M 2016/0027; A61M 2016/1025;
(Continued)

(56) References Cited

U.S. PATENT DOCUMENTS 4,366,821 A * 1/1983 Wittmaier ........... A61M 16/024
600/537
5,367,292 A * 11/1994 Szoke .................. A61B 5/0878
600/529

(Continued)

FOREIGN PATENT DOCUMENTS

WO WO-2009103111 A1 * 8/2009 ............. A61B 5/087
WO 2016106460 A1 7/2016
WO 2018064471 A1 4/2018

*Primary Examiner* — Philip R Wiest
*Assistant Examiner* — Tyler A Raubenstraw
(74) *Attorney, Agent, or Firm* — D'Ambrosio & Menon, PLLC; Usha Menon (57) ABSTRACT

A tracheostomy tube monitor and alerting apparatus includes: (i) a passive humidification device; and (ii) an integrated monitoring assembly fitted in an opening of a rear sidewall of the passive humidification device. The passive humidification device is configured to be connected to a connector of a tracheostomy tube of a patient. Once connected, the monitoring assembly of the apparatus can begin measuring one or more physiological parameters, such as, air flow, oxygen level, carbon dioxide level, pressure, and moisture. The measurements are compared against threshold values that denote blockage or decannulation. When these threshold values are surpassed, an alarm is actuated to alert a caregiver that the patient may be experiencing obstruction or decannulation of the tracheostomy tube.

17 Claims, 5 Drawing Sheets

(51) Int. Cl.
*A61M 16/04* (2006.01)
*A61M 16/08* (2006.01)
A61M 16/16 (2006.01)

(52) U.S. Cl.
CPC ............. *A61M 2016/103* (2013.01); *A61M 2016/1025* (2013.01); *A61M 2205/3576* (2013.01); *A61M 2205/50* (2013.01); *A61M 2205/581* (2013.01); *A61M 2205/583* (2013.01)

(58) Field of Classification Search
CPC ...... A61M 2016/103; A61M 2205/581; A61M 2205/583
See application file for complete search history.

(56) References Cited

U.S. PATENT DOCUMENTS

| | | | | |
|---|---|---|---|---|
| 6,968,841 B2* | 11/2005 | Fini | ..................... | A61M 16/12 128/201.13 |
| 7,428,902 B2 | 9/2008 | Du et al. | | |
| 8,869,793 B1* | 10/2014 | Spandorfer | ....... | A61M 15/0081 128/203.14 |
| 8,925,545 B2* | 1/2015 | Wondka | ............ | A61M 16/0858 128/204.23 |
| 9,101,728 B1* | 8/2015 | Al-Wazzan | ....... | A61M 16/0051 |
| 9,314,579 B2* | 4/2016 | McDaniel | ............ | A61M 16/024 |
| 9,415,182 B2* | 8/2016 | Schneider | .......... | A61M 16/0816 |
| 9,604,027 B2* | 3/2017 | Graham | .............. | A61M 16/0816 |
| 9,987,448 B1* | 6/2018 | Riesberg | ............ | A61M 16/0465 |
| 10,252,018 B2* | 4/2019 | Chaudhry | .......... | A61M 16/0493 |
| 2004/0003814 A1* | 1/2004 | Banner | ............... | A61M 16/042 128/204.21 |
| 2008/0127977 A1* | 6/2008 | Orr | .................... | A61M 16/0858 128/204.22 |
| 2009/0020120 A1* | 1/2009 | Schatzl | ................ | A61B 5/4839 128/204.22 |
| 2011/0120462 A1* | 5/2011 | Tatkov | .................. | A61M 16/16 128/203.14 |
| 2012/0017905 A1* | 1/2012 | Sata | ...................... | A61M 16/16 128/203.26 |
| 2013/0068219 A1* | 3/2013 | Collazo | ................ | A61M 16/20 128/201.13 |
| 2014/0014095 A1* | 1/2014 | Morris | ............... | A61M 16/0465 128/200.26 |
| 2014/0238398 A1* | 8/2014 | Christopher | ........... | A61B 5/087 128/204.22 |
| 2014/0305431 A1* | 10/2014 | Holley | ................ | A61M 16/024 128/205.24 |
| 2015/0283351 A1* | 10/2015 | Castello | ................ | A61B 5/746 600/538 |
| 2016/0136368 A1* | 5/2016 | Spandorfer | ....... | A61M 16/0883 128/203.14 |
| 2017/0021122 A1* | 1/2017 | Wisniewski | .......... | A61M 16/06 |
| 2017/0354793 A1* | 12/2017 | Soliman | ................ | A61M 16/208 |
| 2021/0162153 A1* | 6/2021 | Conrad | ................. | A61M 16/04 |

* cited by examiner

TRACHEOSTOMY TUBE MONITOR AND ALERTING APPARATUS

CROSS-REFERENCE TO RELATED APPLICATION

The present application claims the benefit of the earlier filing date of provisional application Ser. No. 62/692,026 filed on Jun. 29, 2018, entitled "Integrated Alerting and Communication System for Patients with an Artificial Airway," the content of which is hereby incorporated by reference in its entirety.

FIELD OF THE INVENTION

The present application relates to a monitoring and alerting apparatus for patients who have an artificial airway.

BACKGROUND

The trachea is an integral part of the body's airway. The trachea is the windpipe that allows air to flow to the lungs. During inhalation, a normal trachea allows air to travel from the nose to the larynx. The trachea diverges into 2 bronchi, which lead to each lung and allow the organ to refill its oxygen supply. Afterwards, carbon dioxide travels out of the same pathway in the form of an exhale.

Tracheostomy procedures are performed to bypass the upper airway of the patient and restore respiration through the trachea. In the area of pulmonology, tracheostomies provide a means for respiratory support or preventing proximal airway obstruction. These conditions may be caused by throat cancer, tumors, premature birth defects, and sleep apnea, to name a few. Tracheal blockage can occur through mucus buildup, tracheal stenosis from scarring, swelling from inflammation, vocal cord paralysis, neck or head trauma, throat cancer, tumors, premature birth defects that limit respiratory organ function, and sleep apnea. Tracheal blockage occurs in greater than 100,000 patients in the US, and about 100,000 receive life-saving tracheotomies. Of those, 5,000 are children. A tracheostomy tube is installed to assist in airflow after the patient leaves the hospital.

Catastrophic events with tracheostomies occur yearly resulting in death and disability. Since the patient breathes through the tracheostomy tube, a blockage or dislodgment can become an emergency situation. Typical critical events are decannulation and plugging. The removal of the tracheostomy tube is called decannulation. These events often occur at home without proper monitoring. In such a situation, a delayed response by a caregiver may even result in the patient's death. Serious events require immediate action and are preventable.

While tracheostomy procedures are also performed on adults, the risk of death from tube obstruction and accidental decannulation is much lower for adults as they comprehend the danger of what is happening and can ask for help. Children on the other hand sometimes cannot verbally express their distress when they experience complications due to obstruction of the tracheostomy tube or decannulation which are more common in children as they require shorter and narrower cannula. In addition, children are more physically active compared to adults, and may engage in activities that accidentally dislodge the tracheostomy tube. Consequently, the airway would be blocked and their organs, especially their brain would become hypoxic. Unfortunately, a child may not be able to communicate that something is wrong, and thus it is up to the caretaker to detect when a child cannot breathe. However, it only takes about 5 minutes before brain damage occurs and 10 seconds for other organ damage to set in, which can cause lifelong disability if severe. Blockage and/or decannulation of tracheostomy tubes in children results in hypoxia and even death. This is mainly due to lack of communication between the patient and the caregiver when such an event occurs. Children are unable to get the attention of the caregiver when they are in distress, because tracheostomy tubes prevent airflow through the vocal cords which prevents sound from being produced. If the patient, especially small infants are unable to get the attention of the caregiver when they are in distress, a hypoxic event can occur which leads to possible brain damage and even death.

Within the hospital, heavy-duty machines regulate and monitor airflow. The in-hospital monitoring machines are bulky and inconvenient. There is a need for a portable and efficient monitoring machine after the child has been discharged from the hospital that can continually monitor and detect airflow at a patient's tracheostomy tube. Further, traditional monitors are only reactive and not predictive in nature. Caregivers have to constantly watch the patient to make sure that they are breathing normally. Since caregivers are also human, it may not be possible to ensure continual monitoring. There is also a cost involved in providing round the clock bedside monitoring. Also, in the case of certain patients, such as, children, the monitoring is complicated by the fact that the patient may be unable to communicate breathing difficulties to the caregiver. Therefore, there is a need for an automated system for monitoring appropriate airflow and carbon dioxide levels in a patient with an artificial airway.

SUMMARY

The embodiments of the invention are configured to be used in conjunction with a tracheostomy tube in order to monitor and alert caregivers when a patient, and in particular, a pediatric patient, experiences complications due to an obstruction of the tracheostomy tube or decannulation. The various embodiments provide a convenient mechanism for removing the guesswork involved in ensuring that adequate airflow is delivered using a tracheostomy tube. In order to prevent misfortune in infant tracheostomy patients, an integral alarming circuitry can notify caregivers which their child is in distress due to the obstruction or decannulation of the tracheostomy tube. In certain other embodiments, a wireless mobile connected device is provided to continuously monitor breathing in high risk groups.

In one embodiment, an integrated tracheostomy tube monitoring and alerting apparatus is provided for patients with an artificial airway. The system can continually monitor and detect one or more physiological parameters, such as, the airflow and carbon dioxide levels, through the patient's tracheostomy tube. When the apparatus detects that the airflow falls below a predetermined threshold or the carbon dioxide levels exceed or fall below a predetermined threshold, it can automatically communicate the change to a caregiver using one or more alerting means. Since the change may be caused by a blockage in the tracheostomy tube or due to the dislodgment of the tracheostomy tube, the apparatus can facilitate improved response time and can significantly enhance patient safety. The embodiments of the present invention can be used in all patients and, advantageously, with pediatric patients. The embodiments of the invention can monitor the breathing of patients outside of hospitals, in addition to notifying caretakers of any abnormal patterns so that proper action can be taken quickly to avoid hypoxic brain damage and death.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

Various terms are used herein. To the extent a term used in a claim is not defined below, it should be given the broadest definition persons in the pertinent art have given that term as reflected in printed publications and issued patents at the time of filing.

Figure 1:
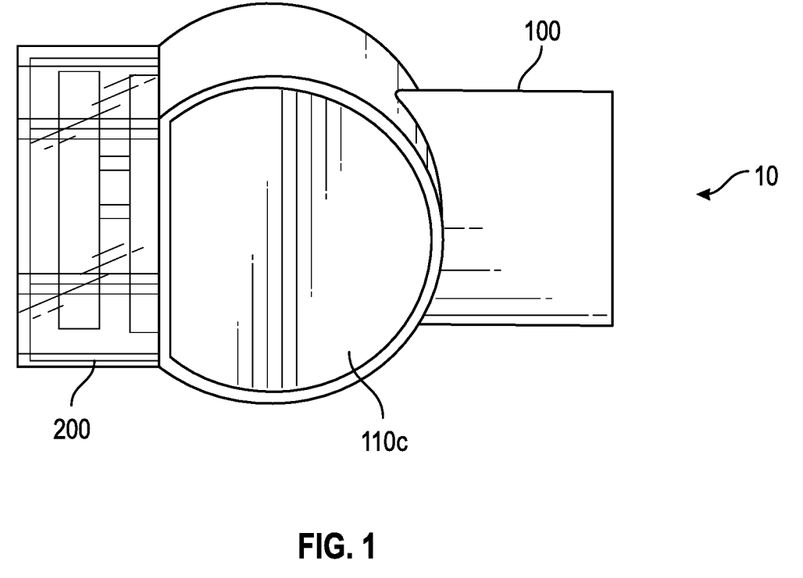
FIG. 1 illustrates an integrated tracheostomy tube monitoring and alerting apparatus according to an embodiment.

FIG. 1 illustrates an integrated tracheostomy tube monitoring and alerting apparatus 10 according to an embodiment. The apparatus 10 is a small/compact, self-contained, light-weight, portable medical device that is configured to provide passive humidification and monitor the airflow in a patient with an artificial airway. Although the various embodiments herein interchangeably use artificial airway and a tracheostomy tube (not shown), it is understood that the artificial airway can also be provided by an endotracheal tube, or other ventilation and aspirating systems. In tracheotomized, spontaneously ventilated patients, the apparatus 10 is configured to be attached to a connector of the artificial airway (not shown) at the tracheal cannula. The apparatus 10 can measure predetermined physiological parameters by monitoring the airflow entering the apparatus. A patient's breathing activity creates a pattern of measured airflow parameters. If the pattern breaks, or in other words, certain measured airflow parameters drop below a threshold, it may be an indication of a blockage or a decannulation. The apparatus 10 is further configured to automatically alert a caregiver in real-time when it detects such an indication of a blockage or a decannulation so that immediate remedial actions can be taken.

Passive humidification devices are commonly used in the care of patients who have had a tracheostomy. The passive humidification device functions as an "artificial nose" when breathing is not possible via the nose, throat or mouth. Passive humidification devices are also known as nose, artificial nose, Swedish nose or Heat and Moisture Exchangers (HME). Using a suitable filter medium, the passive humidification device can store heat and moisture from exhaled air and then emit it back into the air inhaled by the patient. According to an embodiment, the apparatus 10 includes a novel configuration of a passive humidification device ("device") 100 and an integrated monitoring and alerting assembly ("assembly") 200. The device 100 can be made of plastic, silicon or any suitable material. For sanitary reasons and to ensure optimal efficacy, the device 100 is configured as a disposable and replaceable component. Disposability is crucial to maintain a sterilized system, since the device 100 is exposed to saliva and possibly mucus. The device 100 can be replaced daily or as needed. The monitoring assembly 200 is configured as a removable and reusable component that is adapted to be coupled to the device 100.

Figure 2A:
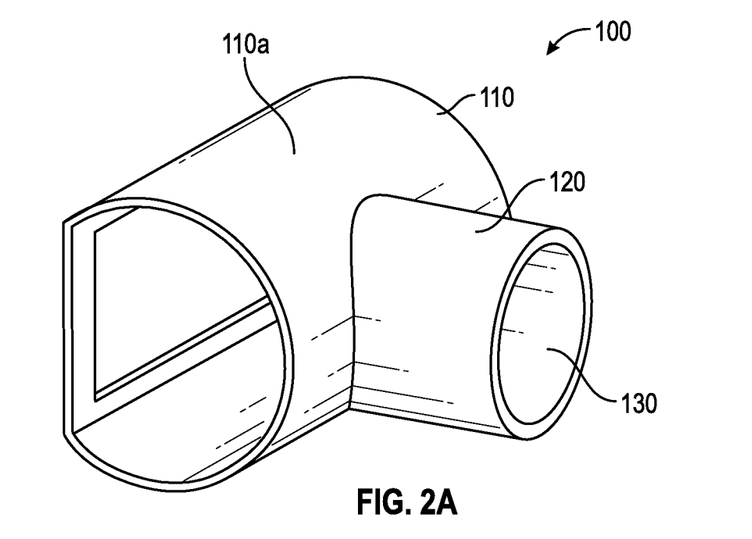
FIGS. 2A-2C illustrate a passive humidification device according to an embodiment.
Figure 2B:
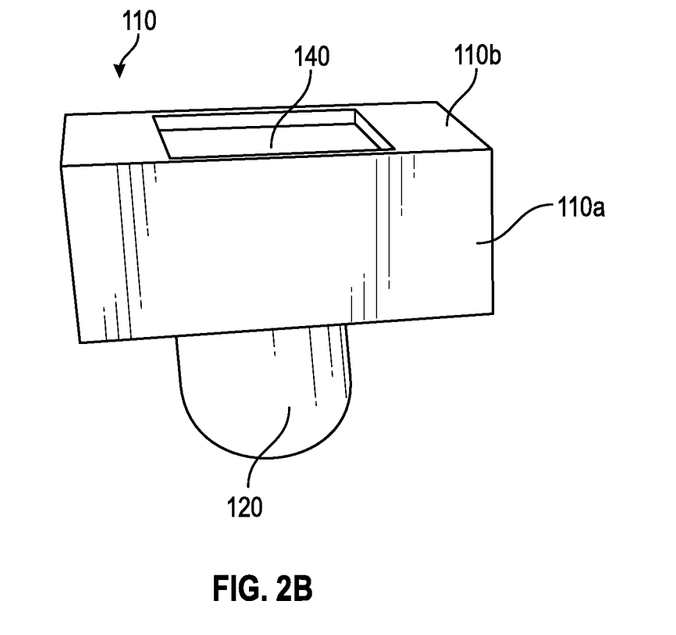
Figure 2C:
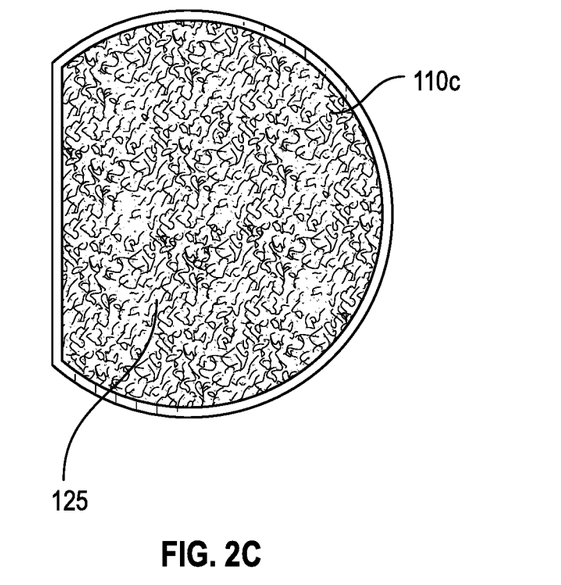

Now referring to FIGS. 2A-2C, the device 100 includes a central housing 110 and a tubular element 120. The central housing 110 defines an enclosure formed by a substantially C-shaped primary sidewall 110a, substantially D-shaped left and right sidewalls 110c flanking a left side and a right side of the primary sidewall 110a and a planar rear sidewall 110b. The tubular element 120 can be configured to protrude from a first face of the primary sidewall 110a. A first end of the tubular element 120 includes a first opening/port 130. Port 130 is adapted to connect to a connector end of a tracheostomy tube of a patient. The port 130 has a generally circular cross-section, conforming to the typical shape and size of a connector of a commonly used tracheostomy tube. The tubular element 120 is connected to the primary sidewall at a second end. The tubular core 120 includes a hollow core which defines a through channel connecting the port and the inside surface of the device 100. The tubular element 120 does not directly contact an inside surface of the semi-circular shaped sidewall of the housing 110A.

FIG. 2C illustrates an inside surface of a left sidewall 110c. The device 100 further includes a right sidewall that is a mirror image of the left sidewall. The left sidewall 110c (and/or the right sidewall) can include a filtering and moisturizing/humidifying medium 125 on its inside surface. When the patient exhales, at least a portion of the exhaled air travels into the device 100 through port 130 and through tubular element 120. The exhaled air contacts the filtering and moisturizing/humidifying medium 125 which is configured to maintain thin secretions and prevent mucus plugs. Filtering and humidifying media are known in the art and can include, without limitation, paper, sponges, ribbons, or foam. In certain embodiments, the medium 125 can be covered in a layer of hygroscopic salt. Heat and moisture from the exhaled air are trapped within the filtering and humidifying medium 125. The heat and moisture can be released back through port 130 when the patient inhales. The filtering and humidifying medium 125 is enclosed within the central housing 110 by the monitoring assembly 200.

Although the embodiments of the invention include an integrated passive humidification device and monitoring assembly, it is envisioned that in another embodiment, the device 100 is devoid of filtering and humidifying media. In such an embodiment, the port 130 can be configured to be coupled to a pre-existing artificial nose ("nose") by cutting out a portion of the nose or to a tracheostomy tube such that the device 100 could be positioned in or over the opening cut in the nose or the tracheostomy tube. The monitoring assembly 200 may then be simply "taped" or otherwise secured to the nose or the tracheostomy tube in such a manner so that the monitoring assembly 200 can detect the airflow and/or carbon dioxide levels in the artificial airway.

As shown in FIG. 2B, an opening 140 is defined within a planar sidewall 110B. The opening 140 can be substantially square-shaped. However, in practice, opening 140 can have any suitable shape. The planar sidewall 110B abuts the semi-circular shaped sidewall of the housing 110A. Opening 140 is axially aligned with port 130. A monitoring assembly 200 can be securely press fitted within the opening 140.

Figure 3:
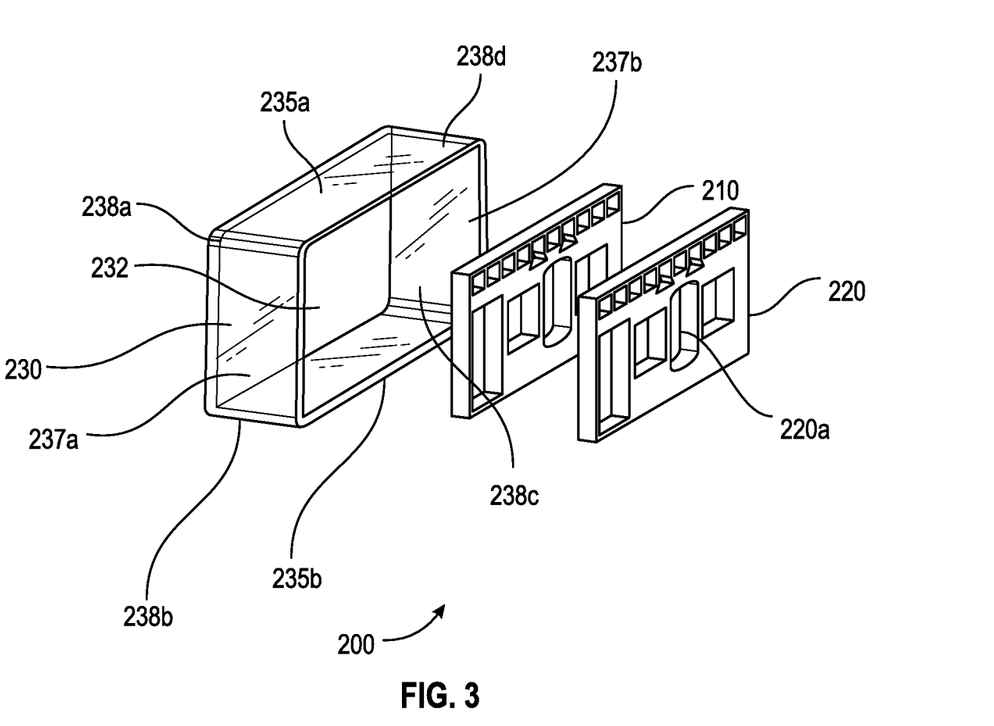
FIG. 3 illustrates a monitoring assembly according to an embodiment.

FIG. 3 illustrates a monitoring assembly 200 according to an embodiment. The monitoring assembly 200 includes a plurality of subcomponents. The three main subcomponents include: a microcontroller 210, a sensor 220 and an alarm/alarm circuitry (not shown). The monitoring assembly 200 further includes a cover 230 for housing the subcomponents. The cover 230 can be made of a transparent/clear material, such as, clear plastic. The cover 230 can include a generally square or rectangular cross section. The cover 230 includes a first planar surface 232. The cover 230 is defined by first 235A and second 235B spaced sidewalls. The first and second sidewalls 235A, 235B are generally parallel to each other. The cover 230 also includes third 237A and fourth 237B spaced sidewalls. The third and fourth sidewalls 237A, 237B are generally parallel to each other and are generally perpendicular to the first and second spaced sidewalls 235A, 235B. The cover 230 is further defined by a first elongate corner 238A interconnecting the first 235A and third 237A sidewalls; a second elongate corner 238B interconnecting the third 237A and second 235B sidewalls; a third elongate corner 238C interconnecting the second 235B and fourth 237B sidewalls; and a fourth elongate corner 238D interconnecting the fourth 237B and first 235A sidewalls. The cover 230 can be dimensioned such its edges can be flush within the opening 140 thereby creating an air-tight barrier for the encased subcomponents. The air-tight seal ensures these subcomponents are protected from inadvertent dislodgement by patient activity. The cover 230 is also configured to prevent any air leakage and pressure loss. In one embodiment, the sensor 220 can be configured to abut and substantially cover the opening 140. A first surface 220*a* of the sensor 220 is exposed to the airflow entering through the port 130.

In or more embodiments, the sensor 220 is a thin sensor. In certain embodiments, the sensor can be a paper-thin sensor configured with inkjet-printed carbon electrodes. The sensor 220 is configured to detect a physiological parameter that is relatively consistent between patients to determine whether there is a blockage of the tracheostomy tube or decannulation, such as, the rate and depth of breathing. The physiological parameters can include, without limitation, pressure, airflow, oxygen concentration, carbon dioxide concentration and/or the moisture content. For instance, the sensor 220 can be configured to detect at least one of: a flow of air moving in and out of the tracheostomy tube, oxygen concentration entering and exiting the tracheostomy tube, carbon dioxide concentration entering and exiting the tracheostomy tube, moisture saturation of the air entering and exiting the tracheostomy tube and pressure of the air entering and leaving the tracheostomy tube.

The sensor 220 can convert the measured airflow parameters into a voltage that can be processed into an electrical signal which can be communicated to the microcontroller 210. In one embodiment, the sensor 220 can be configured to absorb water from 100%-humidified exhaled air and release the water during inhalation of lower-humidity ambient air. Changes in humidity can be detected directly as changes in current. This current signal can be amplified and conditioned by the microcontroller 210. The sensor 220 is operatively coupled to the microcontroller 210.

The microcontroller 210 can include a control board, such as a PCU (Programmable Control Unit) or a PCB (Printed Circuit Board), a battery retainer/slot and a power source/battery (not shown). Any commercially available, long-life battery can be used. The battery supplies power to the microcontroller 210, sensor 220 and other powered components of the monitoring assembly 200. The battery is preferably replaced every time the device 100 is replaced instead of reusing the battery for the duration of its lifetime.

The microcontroller 210 can include electrical/processing circuitry including a data storage unit and a data processor. The microcontroller 210 receives the incoming signal from the sensor 220. The data processor identifies and converts it into a digital signal and then using corresponding software algorithms stored in the data storage unit, converts the digital signal into a value indicative of a measured physiological airflow parameter, such as, pressure. The microcontroller 210 can also compare the measured value in reference to a predetermined threshold for an airflow parameter to determine whether or not to automatically trigger/actuate an alarm. The microcontroller 210 is operably connected to an alarm (not shown).

In one embodiment (not shown), the alarm involves an integrated or built-in audio or audiovisual alarm. The alarm can be connected to a pin of the microcontroller 210. The alarm can include an auditory signal that can be set off if the signal detected by the sensor is below a pressure and/or air flow threshold valye established by code that has been uploaded into the data storage unit of the microcontroller 210.

In certain embodiments, an audible alarm means, such as, a buzzer can be an external to the apparatus. For example, the alarm means can be integrated within a portable monitoring/base station (not shown). The monitoring station may be kept in proximity, such as, within a few meters of the patient. The monitoring station can include an audible, visual or vibrational indicators and/or combinations thereof. The monitoring station can be configured to display predetermined breathing statistics.

In certain embodiments, the microcontroller 210 can communicate measured values to an external display device. For instance, the monitoring assembly 200 may also include a wireless communication circuit (Bluetooth or similar technology) which can facilitate communication with a smart phone, digital display device (not shown) or a monitor remote from the patient, allowing a caregiver to monitor the airflow in an artificial airway of a patient and be alerted.

Figure 4A:
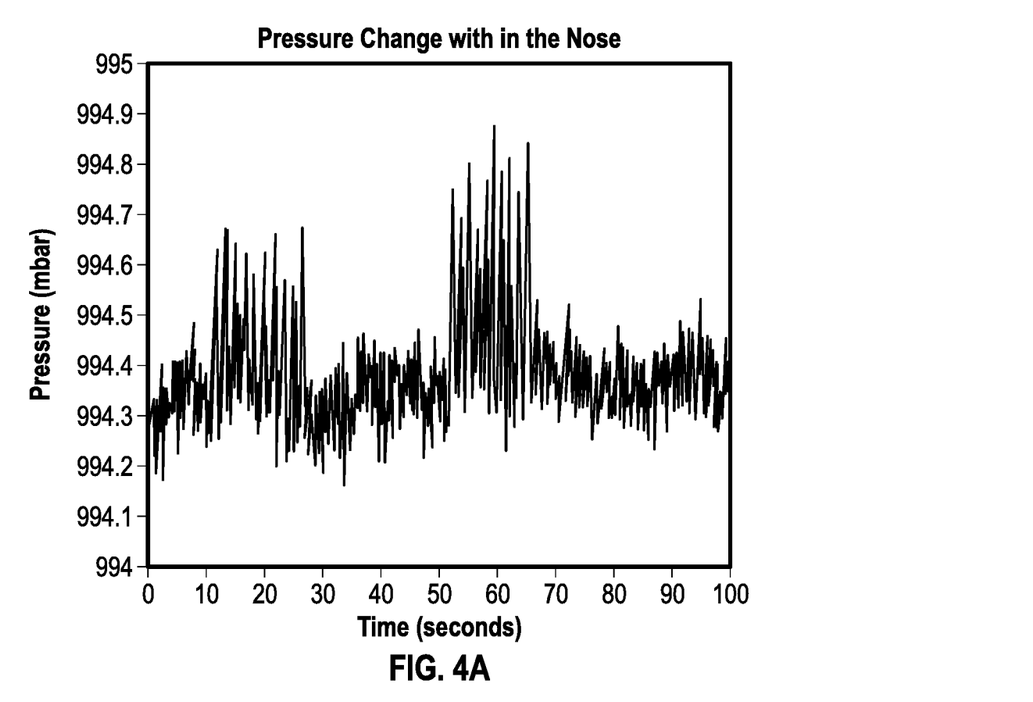
FIG. 4A is a graphical illustration of a pressure change within the apparatus according to an embodiment.
Figure 4B:
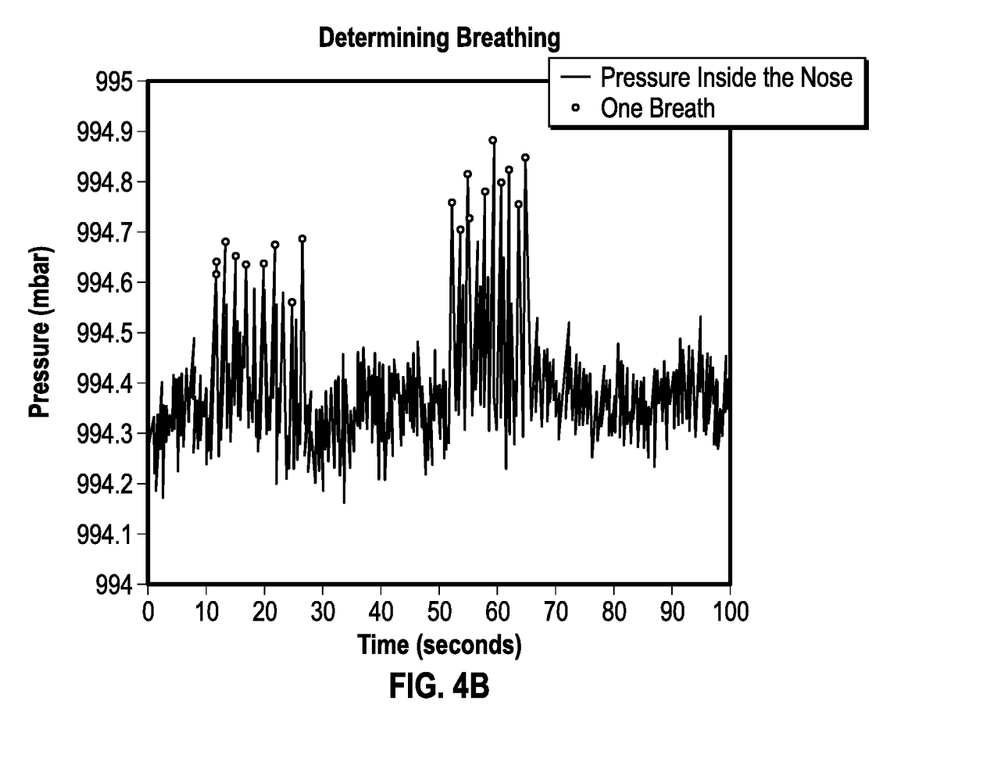
FIG. 4B is a graphical illustration of pressure vs. time to determine breathing according to an embodiment.

As shown in FIG. 4A, breathing can be determined by recorded spikes in the pressure. In a normal patient, when the patient exhales, the pressure increases and goes back to a certain baseline. However, in the event that the pressure remains at baseline for an extended period of time, the microcontroller 210 can determined, using an algorithm, that there can be a blockage or decannulation within the tracheostomy tube. FIG. 4B illustrates a pressure vs. time chart where the peaks are labeled with dots. Each peak is equivalent to a breath. In the event that the microcontroller 220 does not detect pressure spikes, representing breathing, for (say) ten seconds, it can initiate an alerting mechanism causing an alarm to sound thereby indicating that the tracheostomy tube has been blocked or decannulated. As an example, when atmospheric pressure increases, for example, 0.0175%-0.2% above a set baseline, a breath is registered and the microcontroller 210 initiates a built-in timer. The timer can be configured to start counting until another breath is registered or it reaches 10 seconds (or another preset time limit), whichever comes first. If 10 seconds pass without registering a breath, the buzzer can be triggered. The buzzer is configured to be loud enough to be heard by a caregiver nearby. The alarming circuitry can, therefore, provide an alert to a caregiver who may be remote from the patient. The alarm can indicate to the caregiver that the tracheostomy tube has been blocked or decannulated. In other embodiments, the microcontroller 210 can be configured to initiate an auditory, visual, vibrational signal or a combination of these or other known signals in one or more alerting means (such as, buzzers, display monitors, etc.), to alert a caregiver if the measured airflow parameter value is below a threshold value established by the code uploaded onto the microcontroller.

In certain embodiments, the microcontroller 210 can be configured to broadcast the measurements through a measurement communicator (not shown) to a dedicated mobile software application installed on a smart or intelligent device, such as a smart phone or a tablet computer. The application can include software code to analyze the signal, plot and report breathing statistics such as respiration rates. A caregiver may receive an alert or the information from the apparatus 10, including the airflow parameters in an artificial airway of a patient by the dedicated mobile software application.

Figure 5:
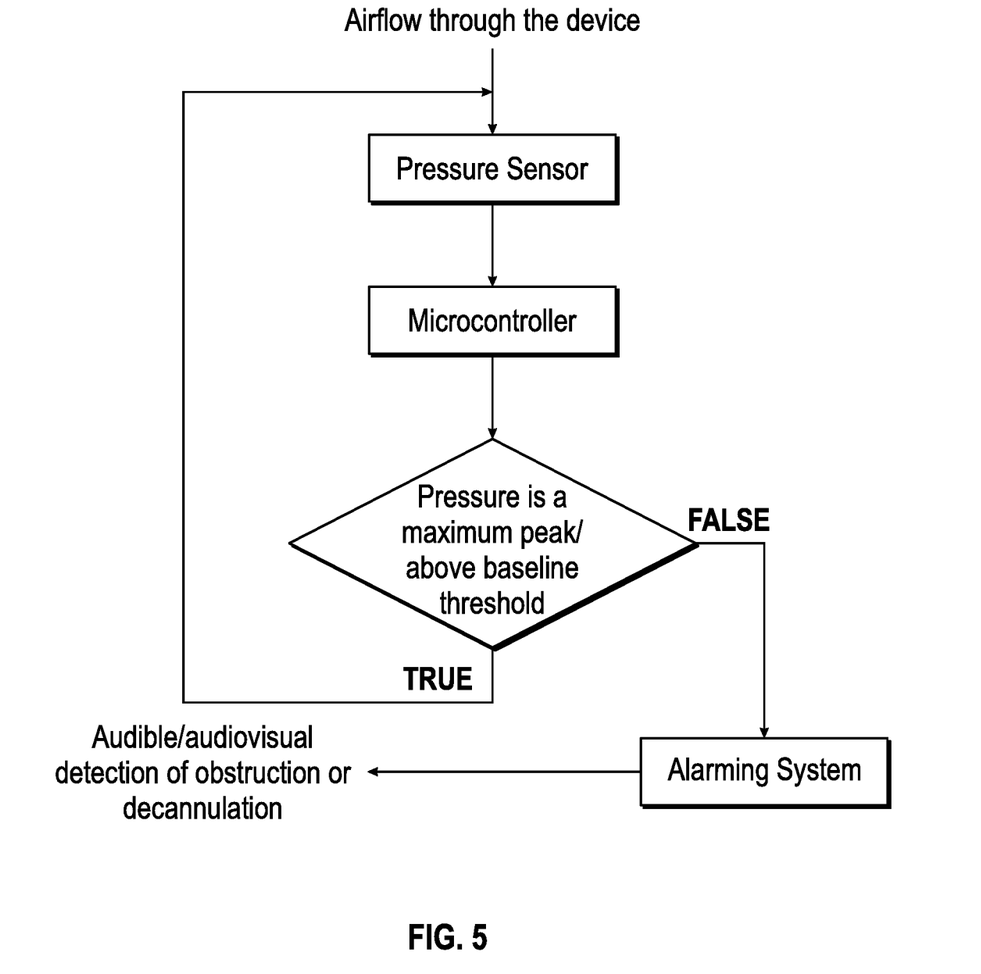
FIG. 5 illustrates an exemplary block diagram according to an embodiment.

An exemplary block diagram is shown in FIG. 5. As shown, the airflow through the passive humidification device of the invention is detected by the subcomponents of the integrated monitoring assembly. The pressure sensor communicates the detected pressure values to the microcontroller. The microcontroller can compare the detected values against a baseline. In one embodiment, the microcontroller can be preconfigured to determine a calibrated threshold value by sampling multiple (for example, over 100) pressure readings in a state of: a) normal breathing, b) obstructed breathing, and c) decannulation to create a baseline. The baseline can be adjusted according to present pressure values. After the baseline is computed, the microcontroller can be able to analyze every breath. As described earlier, each breath can be defined by a maximum peak within a pressure reading that is 0.2% above the calibrated baseline. If no peaks are detected after 10 seconds of pressure acquisition, then an audible alarm can be automatically actuated to denote lack of breath or clogging/decannulation of the tracheostomy tube.

The present invention provides an inexpensive, single patient apparatus and method to continuously or intermittently monitor the airflow and carbon dioxide levels inspired by or delivered to a patient with an artificial airway and a source of controlled air. According to an embodiment, a method for detecting restricted airflow in tracheostomy patients, and particularly, in pediatric patients, is disclosed.

Children have small trachea and, therefore, need smaller tracheostomy tubes. However, these tubes can be blocked or decannulated. As a result, children could suffer from hypoxia and even death. This is mainly due to lack of communication between the patient and the caregiver when such an event occurs. Children may be unable to get timely attention from the caregiver when they are in distress, thus resulting in a hypoxic event leading to possible brain damage and even death.

The method for detecting restricted airflow in pediatric patients involves providing the apparatus discussed herein. The apparatus includes a port which is configured to be connected to the tracheostomy tube without obstructing it or hindering breathing. Once connected, the monitoring assembly of the apparatus is configured to begin measuring one or more physiological parameters, such as, air flow, oxygen level, carbon dioxide level, pressure, and moisture. The measurements are compared against threshold values that denote blockage or decannulation. When these threshold values are surpassed, an alarm (such as, a buzzer) is actuated to alert a caregiver that the patient may be experiencing obstruction or decannulation of the tracheostomy tube. The alarm is triggered automatically and in substantially real-time. The alarm may be a sound, a vibration, or it can be a visual alarm, such as, a light that blinks with increasing frequency or a combination of these or other known features. According to an embodiment, the alert may be configured for a smart or intelligent device, such as, a smart phone. The smart phone may be configured such that when there is, for example, a change in the pressure, it alerts the caregiver with a sound/vibration/buzz or any other known features. In another embodiment, a remote monitoring system is also provided. The remote monitoring system is configured to provide web access and alerts to notify caregivers. The remote monitoring system can include an interface for graphically and numerically tracking the breathing frequency. The remote monitoring system can be configured to process data collected on a plurality of measurements, for example, breathing frequency. The processed data can be custom set to alert devices set up to warn of impending decreased or cessation of airflow. This can also be done with Bluetooth or using another communication means.

Thus, the embodiments of the invention allow caregivers to be alerted instantaneously and in real time on changes to the airflow or carbon dioxide levels without further mathematical manipulation, interpolation, or extrapolation. These changes may be correlated to partial or complete blockages or dislodgment of the tracheostomy tube. This can allow a caregiver to provide attention and any needed rescue and resuscitation in a timely manner which can eventually help to reduce morbidity and also deaths related to tracheostomy.

The apparatus is beneficial for pediatric tracheostomy patients who are discharged from a hospital with a tracheostomy tube. The apparatus enables the patient's caregivers who want to closely monitor the patient's breathing to prevent brain damage or death from breathing complications. For optimal benefit, the caregiver should be near the enough to the patient for the audible alarm to be heard. The caregiver can receive instructions from the patient's doctor on how to respond should such an alarm be triggered. Since the apparatus is connected to a tracheostomy tube, it does not block the tube or hinder the patient's breathing. The apparatus is disposable, portable, inexpensive and parent/caregiver friendly.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. It is, therefore, evident that the particular illustrative embodiments disclosed above may be altered or modified and all such variations are considered within the scope and spirit of the present invention. It should be appreciated by those skilled in the art that the general design and the specific embodiments disclosed might be readily utilized as a basis for modifying or redesigning the apparatus to perform equivalent functions, but those skilled in the art should realize that such equivalent constructions do not depart from the spirit and scope of the invention as described herein.

As used herein, the words "comprise," "have," "include," and all grammatical variations thereof are each intended to have an open, non-limiting meaning that does not exclude additional elements or steps. While the embodiments are described in terms of "comprising," "containing," or "including" various components or steps, the system and methods also can "consist essentially of" or "consist of" the various components and steps. Moreover, the indefinite articles "a" or "an", as used herein, are defined to mean one or more than one of the element that it introduces. If there is any conflict in the usages of a word or term in this specification and one or more patent(s) or other documents that may be incorporated herein by reference, the definitions that are consistent with this specification should be adopted.

I claim:

1. A tracheostomy tube monitor and alerting apparatus, comprising:
   (i) a passive humidification device, the passive humidification device connected to a connector of a tracheostomy tube; and
   (ii) an integrated monitoring assembly, the monitoring assembly fitted within an opening of a rear sidewall of the passive humidification device,
       wherein the opening in the rear sidewall is axially aligned with the connected tracheostomy tube,
       wherein the monitoring assembly includes a plurality of subcomponents, the subcomponents comprising:
       a microcontroller;
       a sensor; and
       an alarm,
       wherein the monitoring assembly includes a cover for encasing the plurality of subcomponents,
       wherein the cover is dimensioned such that its edges are flush within the opening of the rear sidewall thereby providing an airtight seal for the plurality of subcomponents, and
       wherein the cover includes a planar surface and two pairs of opposing sidewalls, and wherein each sidewall is connected to an adjacent sidewall by an elongate corner.

2. The apparatus according to claim 1, wherein the passive humidification device comprises a central housing and a tubular element.

3. The apparatus according to claim 2, wherein the central housing defines an enclosure having:
   a substantially C-shaped primary sidewall;
   a substantially D-shaped left sidewall and a substantially D-shaped right sidewall, the left and right sidewalls flanking a left side and a right side of the primary sidewall; and
   the rear sidewall.

4. The apparatus according to claim 3, wherein the tubular element is configured to protrude from an external surface of the primary sidewall.

5. The apparatus according to claim 4, wherein a first end of the tubular element includes a port, and wherein the port is configured to be connected to the connector of the tracheostomy tube.

6. The apparatus according to claim 5, wherein the tubular element has a hollow core that communicates with an inside surface of the device at a second end.

7. The apparatus according to claim 3, wherein the left and/or the right sidewalls comprise a filtering and humidifying medium, and wherein the filtering and humidifying medium is enclosed within the central housing by the monitoring assembly.

8. The apparatus according to Claim 1, wherein the cover comprises a substantially transparent material.

9. The apparatus according to Claim 1, wherein the sensor is configured to detect at least one physiological parameter within the device.

10. The apparatus according to claim 9, wherein the parameter is selected from the group consisting of: air flow, pressure, oxygen concentration, carbon dioxide concentration, and moisture or humidity content.

11. The apparatus according to claim 10, wherein the sensor is a pressure sensor, and wherein the pressure sensor is configured to detect and measure air pressure changes within the device.

12. The apparatus according to claim 11, wherein the microcontroller is configured to receive and process a signal from the sensor.

13. The apparatus according to claim 9, wherein the microcontroller is operably connected to the alarm.

14. The apparatus according to claim 12, wherein the alarm comprises an audio and/or audiovisual alarm, and wherein the alarm is configured to be actuated when the measured air pressure deviates from a predetermined threshold indicating an occurrence of a blockage or an inadvertent decannulation of the tracheostomy tube, and wherein the threshold is calibrated by multiple sampling during one or more physiological states.

15. The apparatus according to claim 1, wherein the microcontroller is configured to transmit an alert to a smart phone and/or a remote display device.

16. A method of monitoring a pediatric tracheostomy patient, comprising:
   providing a tracheostomy tube monitor and alerting apparatus, comprising:
   (i) a passive humidification device, wherein the opening in the rear sidewall is axially aligned with the connected tracheostomy tube; and
   (ii) an integrated monitoring assembly, the monitoring assembly fitted within an opening of a rear sidewall of the device, wherein the opening in the rear sidewall is axially aligned with a connected tracheostomy tube, wherein the monitoring assembly includes a plurality of subcomponents, a cover for encasing the plurality of subcomponents, wherein the cover is dimensioned such that its edges are flush within the opening of the rear sidewall thereby providing an airtight seal for the plurality of subcomponents, wherein the cover includes a planar surface and two pairs of opposing sidewalls, and wherein each sidewall is connected to an adjacent sidewall by an elongate corner, the subcomponents comprising: a microcontroller, a sensor and an alarm;
   connecting the device to a tracheostomy tube;

monitoring one or more physiological parameters of an airflow entering the device; and automatically triggering an alarm when a parameter deviates from a predetermined baseline value.

17. The method according to claim 16, wherein a deviation from the baseline denotes an obstruction or decannulation of the tracheostomy tube.

\* \* \* \* \*